US00PP11891P2

(12) United States Plant Patent
Chaidez

(10) Patent No.: US PP11,891 P2
(45) Date of Patent: May 22, 2001

(54) ALMOND TREE NAMED 'DURANGO'

(76) Inventor: John Chaidez, 745 W. 11th Ave., Chico, CA (US) 95926

( * ) Notice: Subject to any disclaimer, the term of this patent is extended or adjusted under 35 U.S.C. 154(b) by 0 days.

(21) Appl. No.: 09/069,539

(22) Filed: Apr. 29, 1998

(51) Int. Cl.[7] ..... A01H 5/00
(52) U.S. Cl. ..... Plt./155
(58) Field of Search ..... Plt./155

(56) References Cited

U.S. PATENT DOCUMENTS

P.P. 4,651 * 2/1981 Horton ..... Plt./155
P.P. 5,085 * 8/1983 Bradford ..... Plt./155
P.P. 8,236 5/1993 Spoto .

OTHER PUBLICATIONS

Hortus Third, compiled by the staff of the Liberty Hyde Bailey Hortorium, Macmillan, NY, 1976.*
Wandell, Willet N., Handbook of Landscape Tree Cultivars East Prairie Publishing Illinois, 1989.*
Brochure, The Burchell Nursery, Inc. "Leading the Industry in Growing Trees of Superior Quality", entire brochure.

* cited by examiner

*Primary Examiner*—Bruce R. Campell
*Assistant Examiner*—Wendy A. Baker
(74) *Attorney, Agent, or Firm*—Bernhard Kreten

(57) ABSTRACT

A new and distinct variety of almond tree which is somewhat similar to the 'Peerless' almond tree, but distinguished therefrom by producing fruit that matures three to five days later for harvesting, hulling and shipping than the fruit produced by the 'Peerless' almond tree, and which further produces a high quality fruit of medium size and possessing a soft shell; an important different characteristic from the 'Peerless' variety. Specifically, the 'Peerless' shell requires that a metal cracker be used to remove the kernel from the shell, whereas the 'Durango' kernel can be removed with the use of one's fingers. This new invention has a rich flavor and is comparatively free of doubles (kernels in the shell).

1 Drawing Sheet

BACKGROUND OF THE NEW VARIETY

The present invention relates to a new and distinct variety of almond tree, *Prunus dulcis*, which will hereinafter be denominated varietally as 'Durango', and more particularly to an almond which produces fruit mature for commercial harvesting, hulling and shipment during the fourth week of August to the first week of September in the Orland area of the Sacramento Valley and which is further distinguished as to novelty by producing a soft-shelled almond; the kernel having a flavor characteristic that is excellent compared to 'Peerless' and similar to 'Carmel' with a high percentage of the kernels free of doubles.

There are a number of criteria at which a commercial variety of tree fruit and nuts must excel in order to be a success in the commercial market. Among these are ripening date, flavor, texture and shipping quality. With tree fruits and nuts such as almonds the early ripening date, the quality of the meat of the kernel, freedom from an unusual number of doubles, and more particularly, a soft shell makes this new almond commercially attractive and thereby appealing to the distributor and the consumer; thus providing a substantial likelihood of success.

Almond varieties are characterized as to soft shell or hard shell; the latter characteristic makes nut (kernel) removal difficult and hard to market because of the nature of the shell, i.e., it is difficult to crack. In addition, the variations in maturity dates vary considerably—approximately six weeks—thereby providing long harvesting, hulling, and shipping seasons. Most particularly in almond varieties of tree fruits the ease of shelling and the high quality of the kernel plus a very low percentage of doubles provides an excellent appeal to the distributor and consumer.

ORIGIN AND ASEXUAL REPRODUCTION OF THE NEW VARIETY

The present invention of almond tree hereof was discovered by the inventor in his orchard which is located on the east side of Road S and south side of Road 25, approximately five miles southeast of the town of Orland, Calif.

The variety was discovered as an open pollinated seedling growing as a volunteer near a 'Peerless' almond planting in the late 1980's to possibly 1990. After several years of observation the inventor had the new invention asexually propagated by budding and/or grafting on fifty-four trees of peach (Lovell) root in the vicinity of Orland, Calif. in 1992 through 1993. These trees have been observed over the past three years by the inventor and are confirmed to be identical to the original tree of the new variety. Fifty-four trees resulted from the first asexual propagation. The progeny did not display any changes morphologically from the parent plant. The trees are in their 4th leaf and the vigor of this new variety is similar to the vigor of the 'Peerless'.

SUMMARY OF THE NEW VARIETY

The 'Durango' almond tree is characterized by producing a soft shelled almond which resembles the 'Peerless' almond but has some of the varietal characteristics of the 'Carmel' variety. The fruit (nuts) produced by the 'Durango' variety is ripe for commercial harvesting, hulling and shipping approximately in the fourth week of August to the first week of September. The new and novel variety, as stated earlier, is perhaps most closely similar to the 'Peerless' but distinguishes therefrom as to the soft shell nature and it is harvested two to five days later than 'Peerless'. The nut weight is similar to the 'Peerless' variety of almond. The new variety is equal to or slightly larger than the 'Peerless' variety with a high quality and high percentage of meat weight as compared to the total weight of the almond in shell (69%). The low percentage of doubles in the shell (0.4%) is an excellent characteristic. Although this new invention somewhat resembles the kernel quality of the variety 'Carmel', the meat of the kernel is light colored, similar to the 'Peerless' variety.

BRIEF DESCRIPTION OF THE DRAWING

The drawing is a color photograph (taken from material collected in the field, and mailed that same day to a commercial photographer, but received the following day resulting in a photograph as close as is reasonably possible to attain in a color photographic illustration of this type) showing the mature fruit (nuts in this case) of the new variety of almond tree of the present invention including the following details: the first view, the fruit with the husks on and in various stages of splitting; the second view, the nuts without the husks, displaying the shape of the shell fruit in side view; the third view, displays the shelled fruit with the suture up; the fourth view, displays the unshelled nut in side view to display the shape of the nut; the fifth view, of the nut, shows the side up; and finally, there is a view of the foliage with fruit attached and the young terminal branches.

DETAILED DESCRIPTION

Referring more specifically to the pomological details of this new and distinct variety of almond tree, the following has been observed under the ecological conditions prevailing at the designated orchard of origin near Orland, Calif. All major color codes designations are by reference to the Dictionary of Color by Maerz and Paul, First Edition, published in 1930.

Tree

Generally:

*Origin.*—Open pollinated volunteer, found growing near a 'Peerless' planting.

*Vigor.*—Vigorous and Hardy.

*Chilling.*—Grown under typical Northern California Sacramento Valley climatic conditions.

*Figure.*—Moderate and spreading to Upright growth; crotch angles vary from 30 to 45 degrees.

*Productive.*—Very productive (prolific).

*Regularity of bearing.*—Regular.

Trunk:

*Size.*—Medium in diameter.

*Surface texture.*—Coarse.

*Color.*—Bark — Pg. 38 Pl 8H — Pl 7H.

*Lenticel.*—Numerous.

*Lenticel size.*—Medium.

Branches:

*Size.*—Medium.

*Surface textures.*—Relatively smooth.

*Color.*—One year or older — Pg. 34 Pl 6 8C. Immature — Pg. 60. Pl. 19-8D. Surface texture — smooth.

Leaves:

*Size.*—Length 92–115 MM (3.62–4.72 inch). Width 33–43 MM (1.30–1.69 inch). Thickness — Average for almond.

*Form.*—Lanceolate.

*Color.*—Upward disposable surface — Pg. 66 Pl. 22 E8 (Civette Green). Downward disporable surface — Pg. 64 Pl. 21I7 (Fern Green).

*Leaf vein.*—Color — Pg. 62 Pl. 20 K1 (Russett Green).

*Marginal form.*—Crenulate.

*Glands.—Small* — 2–3 globose is same in form on opposite side of leaf.

*Petiole.*—Length — 21 MM–25 MM (0.83–0.98 inch). Thickness — average — 2 MM (0.0788 inch). Color — p. 62 Pl. 20 K1 (Russet Green). Stipules — None.

Flowers:

*Date of first bloom.*—Feb. 19–20, 1998 (15–20%). Showy and numerous; need pollinators.

*Size.*—Width — 15–23 MM (0.59–0.91 inch diameter).

*Petals.*—Five — 8–10 MM long (0.31–0.39 inch).

*Stamens.*—16–24 — 3–6MM (0.1–0.24 inch long).

*Pistil.*—1 small 6 MM (0.24 inch long).

*Color code.*—White.

*Flowers per cluster.*—2 to 3.

Fruit

Maturity when described: Ripe for commercial harvesting, hulling and shipment fourth week of August to first week of September.

Size:

*Generally.*—Medium size

*Average diameter of in shell (unhulled fruit).*—17 MM— 21 MM — (0.47–0.83 inch). Length 32–34 MM (1.26–1.34 inch). Thickness 14–77 MM (0.55–0.67 inch).

*Average diameter shelled nuts.*—12–14 MM (0.47–0.55 inch) Length 22–25 MM (0.87–0.98 inch) Thickness 8–10 MM (0.34–0.39 inch)

*Form.*—Uniformity — shell and kernel are uniform in shape. Symmetry — somewhat asymmetrical (ovate) — both unhulled shells and shelled nuts with one side more curved than the other, one side of shell has a keel, similar to 'Peerless' in shape.

*Suture.*—Minimal (kunel).

*Stem cavity.*—None.

*Stem.*—(i.e., attachment of the fruit to the branch — peduncle) short and thick.

*Color.*—Similar to color of the immature branch (less than 2 years old) Pg.60,Pl. 19-8D

*Apex.*—Acute.

*Base.*—Slightly rounded both in the shell and shelled.

*Skin.*—On nuts practically nonexistent.

*Skin coloration on kernel.—Pg.* 30 Pl. 4 I8 (Colonial Rose).

*Coloration of hull (outer).*—Pg. 96 Pl. 37 A2 (New Silver).

*Color of shell.*—Pg. 28 Pl. 3 B7 (Iris Mauve) to Pg. 30 Pl. 4 C9 (Polignac).

*Flavor.*—Good, rich.

*Aroma.*—Pleasant.

*Texture.*—Firm.

*Fibers.*—None.

*Ripening.*—Normal for almonds.

*Number.*—Total of 400 meats (kernels) per pound.

*Eating quality.*—Excellent.

The following is a description of the "shell" in which the kernel is found:

*Attachment.*—None, the hull can be easily removed manually.

*Fibers.*—None.

*Fibers length.*—None.

*Size.*—Described under Fruit Section.

*Form.*—Ovate.

*Apex.*—Pointed.

*Color.*—Of dried kernel Pg 30. Pl. 4 8E-8I (Colonial Rose).

*Base.*—Generally rounded.

*Sides.*—Smooth, slightly unequal.

*Hilium.*—Insignificant.

*Tendency to split.*—None observed.

*Use.*—Fresh market, et al.

*Keep quality.*—Very good, under field storage conditions lacking temperature and humidity controls, no fungal or bacterial disease problems have been encountered to date.

Resistance to disease: No susceptibilities noted. However, because of early bloom, it may be susceptible to frost damage to the flowers (bloom)

Pollination requirements: 'Peerless' variety of almond, no incompatibility with other almond varieties as pollinators

LAST STATEMENT

Although the new variety of almond tree possesses the described characteristics noted above as a result of the growing conditions prevailing in the Orland area of the Sacramento Valley of Northern California, it is to be understood that variations of the usual magnitude and characteristics incident to changes in growing conditions, fertilization, pruning and pest control are to be expected.

Having thus described and illustrated my new variety of almond tree, which I claim as a new and desired to be secured by Plant Letters Patent is:

1. A new and distinct variety of almond tree as herein illustrated and described, and which is somewhat similar to the 'Peerless' and yet varietally similar to the 'Carmel' almond but is distinguished therefrom and characterized principally as to novelty by producing fruit (nuts) which are mature commercially for harvesting, hulling, and shipping during the last week of August and the first week of September in the Sacramento Valley of Northern California, which has excellent flavor, and which has a soft shell, making hulling very easy and is a highly marketable nut with very few doubles, and a high percentage of meat weight in the shell with a light brown color and excellent keeping qualities.

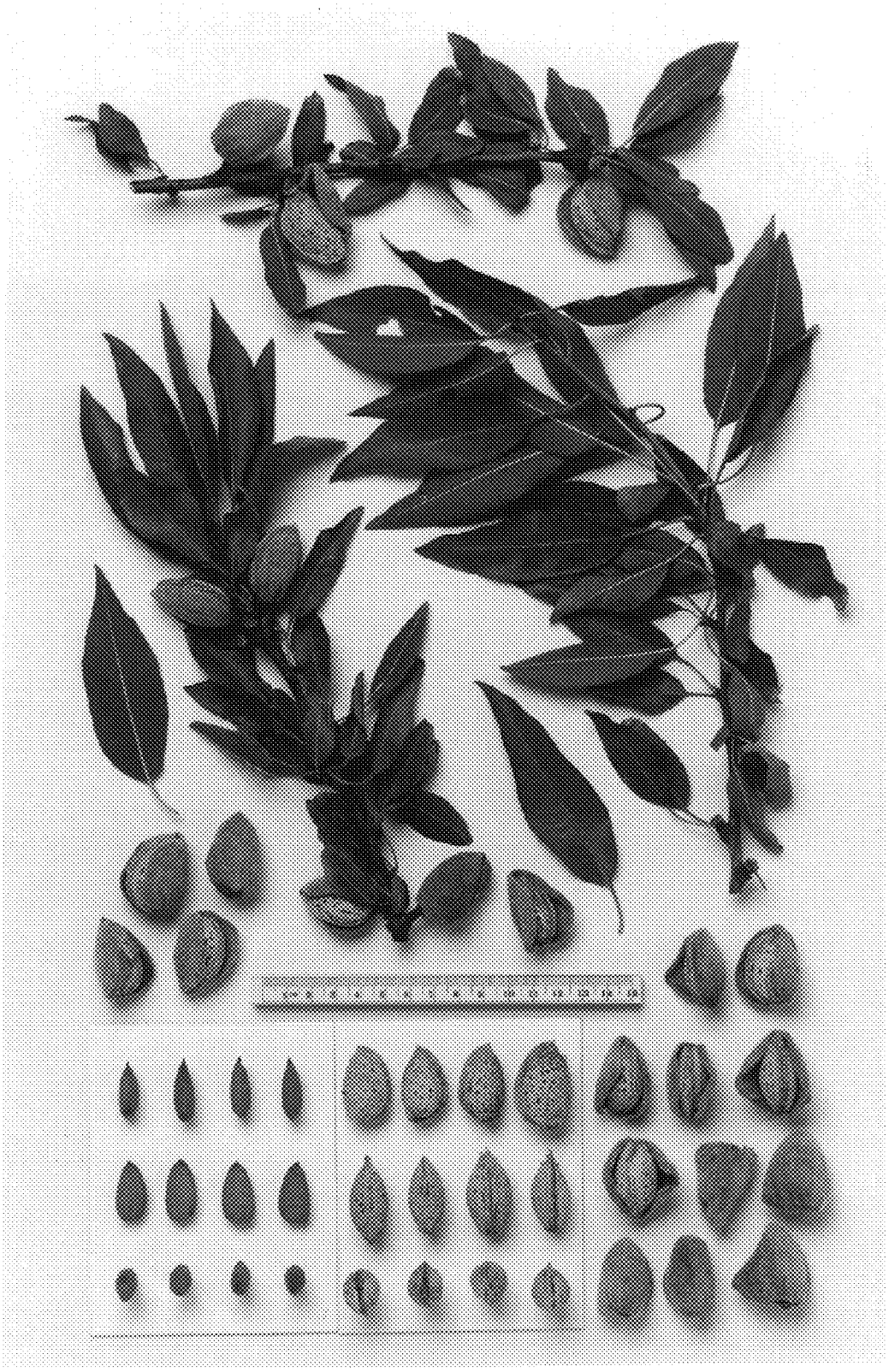

* * * * *